US010485615B2

(12) United States Patent
Sela et al.

(10) Patent No.: US 10,485,615 B2
(45) Date of Patent: Nov. 26, 2019

(54) MEDICAL ELECTRONIC DEVICE WITH MULTI-TRACKING CAMERAS

(71) Applicants: Gal Sela, Toronto (CA); Kamyar Abhari, Toronto (CA); Dorothy Lui, Toronto (CA); Kai Michael Hynna, Toronto (CA); Kirusha Srimohanarajah, Toronto (CA)

(72) Inventors: Gal Sela, Toronto (CA); Kamyar Abhari, Toronto (CA); Dorothy Lui, Toronto (CA); Kai Michael Hynna, Toronto (CA); Kirusha Srimohanarajah, Toronto (CA)

(73) Assignee: Synaptive Medical (Barbados) Inc., High Street, Bridgetown (BB)

( * ) Notice: Subject to any disclaimer, the term of this patent is extended or adjusted under 35 U.S.C. 154(b) by 170 days.

(21) Appl. No.: 15/638,431

(22) Filed: Jun. 30, 2017

(65) Prior Publication Data
US 2019/0000556 A1    Jan. 3, 2019

(51) Int. Cl.
*A61B 34/20*      (2016.01)
*A61B 34/30*      (2016.01)
*A61B 34/00*      (2016.01)
A61B 34/10      (2016.01)

(52) U.S. Cl.
CPC .............. *A61B 34/20* (2016.02); *A61B 34/30* (2016.02); *A61B 34/74* (2016.02); *A61B 2034/107* (2016.02); *A61B 2034/2055* (2016.02); *A61B 2034/2065* (2016.02); *A61B 2034/301* (2016.02)

(58) Field of Classification Search
CPC ... A61B 34/20; A61B 34/30; A61B 2034/107; A61B 2034/2055; A61B 2034/2065
See application file for complete search history.

(56) References Cited

U.S. PATENT DOCUMENTS

| 2001/0039421 | A1 | 11/2001 | Heilbrun et al. |
| 2013/0010081 | A1 | 1/2013 | Tenney et al. |
| 2015/0351860 | A1* | 12/2015 | Piron ................... A61B 5/0095 |
| | | | 600/417 |

FOREIGN PATENT DOCUMENTS

WO    2014139019 A1    9/2014

OTHER PUBLICATIONS

Search report issued by the Intellectual Property Office of the United Kingdom in relation to corresponding GB application No. GB1810564.3 dated Feb. 14, 2019, 4 pgs.

* cited by examiner

*Primary Examiner* — Toan M Le
(74) *Attorney, Agent, or Firm* — Rowand LLP

(57) ABSTRACT

In one aspect, a medical tracking system is described. The medical tracking system includes a first tracking system providing a first tracking region. The first tracking system is configured to track a tracked instrument within the first tracking region. The medical tracking system further includes a second tracking system providing a second tracking region. The second tracking system is configured to track the tracked instrument within the second tracking region. The medical tracking system also includes a processor coupled to the first tracking system and the second tracking system. The processor is configured to determine, based on data received from the first tracking system and data received from the second tracking system, transposition information to map data received from the first tracking system and data received from the second tracking system into a common space.

18 Claims, 6 Drawing Sheets

MEDICAL ELECTRONIC DEVICE WITH MULTI-TRACKING CAMERAS

TECHNICAL FIELD

The present application relates to medical electronic devices and, more particularly, to medical electronic devices having tracking capabilities for tracking markers.

BACKGROUND

Medical electronic devices sometimes use a tracking system to provide tracking of an object or patient within a procedure room, such as an operating room. The tracking system may track tracking markers that are provided on a medical instrument, for example. By tracking the tracking markers, the medical electronic device can determine the location, in space, of the tracked tool or instrument. This location information may be used, for example, to facilitate a medical procedure. For example, in some embodiments, the location of the tracked tool or instrument may be used to automatically reposition a robotic arm associated with the medical electronic device. Other functions are also possible.

In some instances, an operator, such as a doctor or nurse, may interfere with the tracking of the tracked tool or instrument by the medical electronic device. For example, the operator may orient themselves between the tracking system and the tracked instrument or tool, causing the tracking system to lose tracking of the tracking tool or instrument.

SUMMARY

In one aspect, the present disclosure describes a medical tracking system for identifying a position of a tracked instrument having a plurality of tracking markers provided thereon. The medical tracking system includes a first tracking system providing a first tracking region. The first tracking system is configured to track the tracked instrument within the first tracking region. The medical tracking system further includes a second tracking system providing a second tracking region. The second tracking system is configured to track the tracked instrument within the second tracking region. The medical tracking system also includes a processor coupled to the first tracking system and the second tracking system. The processor is configured to determine, based on data received from the first tracking system and data received from the second tracking system, transposition information to map data received from the first tracking system and data received from the second tracking system into a common space.

In yet a further aspect, the present disclosure describes a processor coupled with a first tracking system and a second tracking system. The processor is configured to receive, data from the first tracking system. The first tracking system is providing a first tracking region and the first tracking system is configured to track a tracked instrument within the first tracking region. The processor is further configured to receive data from the second tracking system. The second tracking system is providing a second tracking region. The second tracking system is configured to track the tracked instrument within the second tracking region. The processor is further configured to determine, based on data received from the first tracking system and data received from the second tracking system, transposition information to map data received from the first tracking system and data received from the second tracking system into a common space.

In yet a further aspect, the present disclosure describes a non-transitory processor-readable storage medium. The non-transitory processor-readable storage medium includes processor-executable instructions which, when executed, configure the processor to: receive, data from a first tracking system, the first tracking system providing a first tracking region and the first tracking system configured to track a tracked instrument within the first tracking region; receive data from a second tracking system, the second tracking system providing a second tracking region, the second tracking system configured to track the tracked instrument within the second tracking region; and determine, based on data received from the first tracking system and data received from the second tracking system, transposition information to map data received from the first tracking system and data received from the second tracking system into a common space.

Other aspects will be understood by a person skilled in the art in view of the disclosure and accompanying drawings.

BRIEF DESCRIPTION OF THE DRAWINGS

Embodiments will now be described, by way of example only, with reference to the drawings, in which.

DETAILED DESCRIPTION

Figure 1:
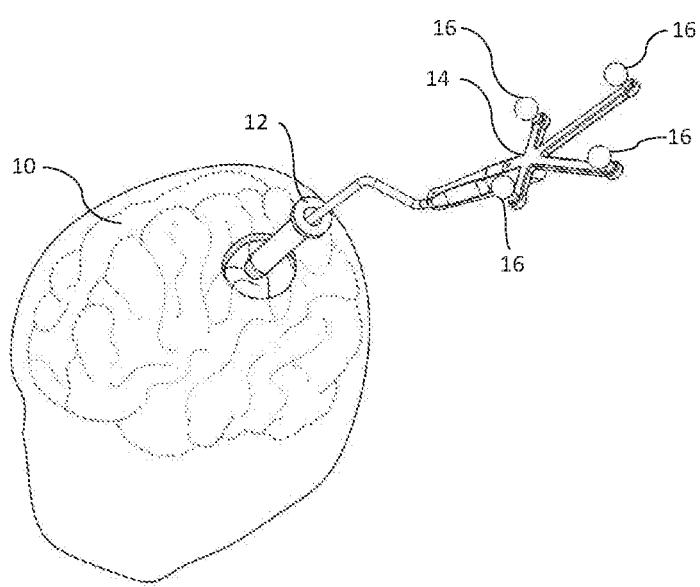
FIG. 1 is a perspective view illustrating insertion of an access port into a brain and a medical instrument in accordance with example embodiments of the present disclosure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

As used herein, the term "processor" is intended to include both single processors and multiple processors operating together.

Unless defined otherwise, all technical and scientific terms used herein are intended to have the same meaning as commonly understood by one of ordinary skill in the art. Unless otherwise indicated, such as through context, as used herein, the following terms are intended to have the following meanings.

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein, the term "tracked instrument" describes any tool, instrument, fixture that is configured to be tracked using a tracking system associated with a medical electronic device. The tracked instrument may, in some embodiments, be a pointer.

As used herein, the term "tracking system" describes a system that is configured to track an object in space. A "tracking system" is defined to include one or more sensors, such as two image sensors placed in spaced relation to one another to allow depth information for a tracked object to be obtained. For example, stereoscopic principles may be relied upon to determine a distance of the tracked object relative to the tracking system or to some arbitrary coordinate system. A tracking system may, therefore, include two or more camera elements (i.e., two or more image sensors) or other sensors. The tracking system may rely on various tracking technologies including, for example, infrared tracking technologies, magnetic tracking, video based tracking, inertial tracking, etc.

Medical tracking systems are described herein which include two or more tracking systems. Example medical tracking systems are described in greater detail in the description which follows.

An example of one possible "tracked instrument" will now be discussed, with reference to FIG. 1. FIG. 1 illustrates a port-based surgery facilitated by a tracked instrument. In the example of a port-based surgery, a surgeon or robotic surgical system may perform a surgical procedure involving tumor resection in which the residual tumor remaining thereafter is minimized, while also minimizing the trauma to the healthy white and grey matter of the brain. A beneficial input that may assist minimization of residual tumor and healthy tissue damage may be visualization of the area of interest using high resolution optical coherence tomography (OCT) imaging providing a greater capacity to resolve the unhealthy brain tissues.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO BrainPath. Surgical tools and instruments may then be inserted within the lumen of the access port in order to perform surgical, diagnostic or therapeutic procedures, such as resecting tumors, as necessary. The present disclosure applies equally well to catheters, deep brain stimulation (DBS) needles, a biopsy procedure, and also to biopsies and/or catheters in other medical procedures performed on other parts of the body where head immobilization is needed.

In the example of a port-based surgery, a straight or linear access port 12 is typically guided down a sulcal path of the brain. Surgical instruments 14 may then be inserted down the access port 12.

In the example of FIG. 1, the surgical instrument 14 is a tracked instrument, which has features allowing it to be tracked by a tracking system. More particularly, the tracked instrument includes a plurality of tracking markers 16. The tracking markers are, in the example, tracking spheres. In the example embodiment, the tracked instrument includes four reflective tracking spheres. The tracking markers are provided on the tracked instrument in a known configuration. That is, the tracking markers are provided on the tracked instrument in a configuration that is known to a medical electronic device which tracks the tracked instrument. Using this known geometry, the medical electronic device can determine the location of other features of the tracked instrument, such as the tip of the tracked instrument.

Accordingly, optical tracking systems, which may be used in the medical procedure, track the position of a part of the tracked instrument that is within line-of-site of the optical tracking system. These optical tracking systems may use a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked. It should be noted that embodiments provided herein which employ an optical tracking system may be extended to any relevant tracking system as are known in the art.

Figure 2:
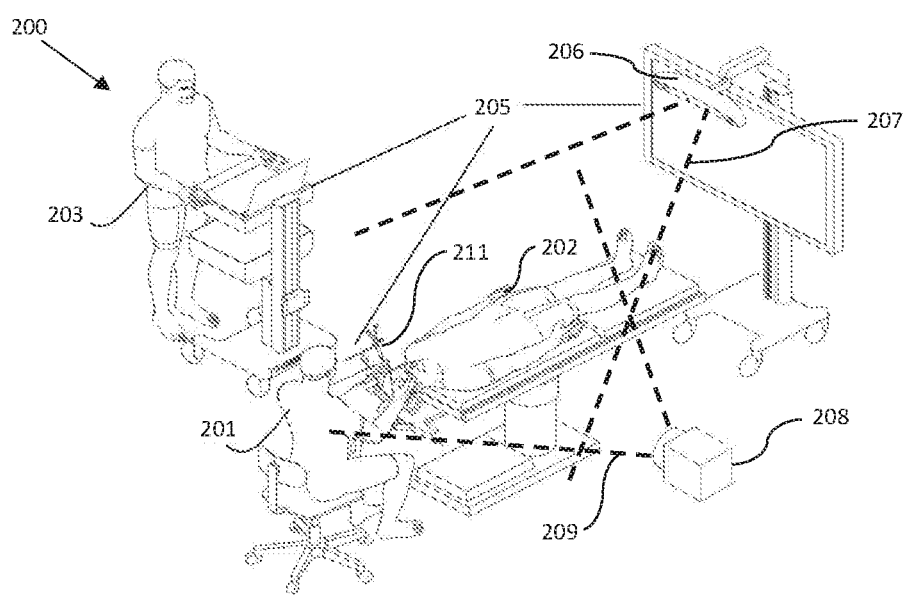
FIG. 2 is a perspective view of a medical procedure room in which a medical electronic device in accordance with example embodiments of the present disclosure is used.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system (which is an optical tracking system in the embodiment of FIG. 2), displays and tracked instruments 211 assist the surgeon 201 during his procedure. An operator 203 is also present to operate, control and provide assistance for the medical navigation system 205. A detailed description of a surgical navigation system is outlined in international application PCT/CA2014/050270, entitled "SYSTEMS AND METHODS FOR NAVIGATION AND SIMULATION OF MINIMALLY INVASIVE THERAPY", which claims priority to U.S. Provisional Patent Application Ser. Nos. 61/800,155 and 61/924,993, which are all hereby incorporated by reference in their entirety.

The tracking system of FIG. 2 is a medical tracking system which may be used for identifying a position of a tracked instrument, such as a tracked instrument of the type described above with reference to FIG. 1. The medical tracking system of FIG. 2 includes a first tracking system 206 which acts as a primary tracking system. The first tracking system 206 is providing a first tracking region 207. The first tracking region 207 is a region in front of the first tracking system 206 that the first tracking system 206 is able to observe. That is, the first tracking region 207 is an area that is represented in data generated by the first tracking system 206. The first tracking system 206 is configured to track the tracked instrument within the first tracking region.

Since a tracking system, such as the first tracking system, may include multiple image sensors, each with their own respective field of view, the tracking region for a tracking system may be based on one or more such field of views for the individual image sensors. For example, where the tracking region for a tracking system may be the intersection of the field of views for the individual image sensors. For example, the tracking region may be the portion of the individual field of views that overlaps. By way of further example, in some embodiments in which there are more than two image sensors in a tracking system, the tracking region may include the intersection or union of the field of view for any two image sensors.

In the example illustrated, the first tracking system 206 is provided on a fixture that is positioned in a medical procedure room, such as an operating room. In the example illustrated, the first tracking system 206 is positioned near the foot of a hospital bed. The first tracking system 206, in the example, provides a first tracking region 207 that includes a patient's head and space near the patient's head. In this manner, the first tracking system 206 may be used to facilitate brain surgery.

The first tracking system 206 may be used by the medical electronic device for any one of a number of medical uses. By way of example, in some embodiments, the first tracking system 206 may be used during a patient registration procedure. In some such embodiments, during the patent registration procedure an operator may place a tracked instrument 211 (such as a pointing tool) at certain predetermined locations associated with a patient. For example, fiducial points may be identified on images and then the tracked instrument may be used to touch the associated locations. By observing the tracked instrument 211 during the patient registration procedure, the medical electronic device may determine the location of the patient 202 in space. This allows the medical electronic device to map the physical coordinate space of the operating room to the image space of the magnetic resonance imaging (MRI) image, computerized tomography (CT) image, or image of another type.

The tracked instrument may be used for other purposes instead of or in addition to patient registration. For example, in some embodiments, the tracked instrument may act as an input mechanism to control or reposition a robotic arm associated with the medical electronic device. The robotic arm may, for example include a camera disposed thereon which provides imaging during a medical procedure.

Other uses of the tracked instrument are also contemplated.

In some instances, the tracked instrument 211 may be occluded to the first tracking system 206. For example, an operator 203 or surgeon 201 may inadvertently obstruct the tracked instrument 211. By way of example, a surgeon 201 may place their hand between the first tracking system 206 and the tracked instrument 211 in such a manner that the tracked instrument 211 is not visible to the first tracking system 206. In such circumstances, if the medical electronic device were to rely solely on the first tracking system 206 for tracking the tracked instrument 211, the medical electronic device may lose tracking of the tracked instrument when the tracked instrument 211 is occluded.

In the embodiment of FIG. 2, the medical electronic device includes a second tracking system 208. The second tracking system 208 is providing a second tracking region 209. The second tracking region 209 may partially overlap with the first tracking region 207. That is, the second tracking region 209, in the illustrated example, include at least a portion of the first tracking region. The second tracking system 208 is configured to track the tracked instrument within the second tracking region.

Since there is, in the illustrated example, some overlap between the first tracking region and the second tracking region, the first tracking system and the second tracking system may provide redundancy. This redundancy may improve tracking of the tracked instrument when the tracked instrument is obscured. Further, this redundancy may improve tracking of the tracked instruments even when the tracked instrument is visible to both the first tracking system and the second tracking system. That is, the accuracy of position detection may be improved in at least some circumstances through the use of multiple tracking systems.

While FIG. 2 illustrates only two tracking systems, in other embodiments, a greater number of tracking systems may be used. For example, in some embodiments, the medical tracking system may include three or more tracking systems.

In some embodiments, the first tracking system 206 is fixedly mounted within the medical procedure room while the second tracking system is movable within the medical procedure room. That is, the first tracking system 206 is a stationary camera while the second tracking system 208 is a movable tracking system. The second tracking system 208 may, for example, be a re-positionable camera which may be selectively positioned at a desired location within the medical procedure room by an operator 203. For example, the second tracking system 208 may be repositioned based on the location of a surgeon 201 (e.g., to position the second tracking system 208 in a location where tracking of the tracked instrument by the second tracking system 208 is unlikely to be affected by a surgeon).

The first tracking system 206 and the second tracking system 208 are tracking systems (such as tracking cameras, for example) that are configured to track tracking markers. In at least some embodiments, the tracking systems may be infrared tracking systems. Such tracking systems may include an infrared emitter which is configured to periodically emit infrared radiation in a respective tracking region. For example, the first tracking system may include a first emitter which is configured to emit radiation in the first tracking region. The tracking systems may track the tracking markers and, more particularly, the tracked instrument, based on light reflected. That is, the tracked instrument may be tracked based on the light reflected from the tracking markers on the tracked instrument.

Figure 3:
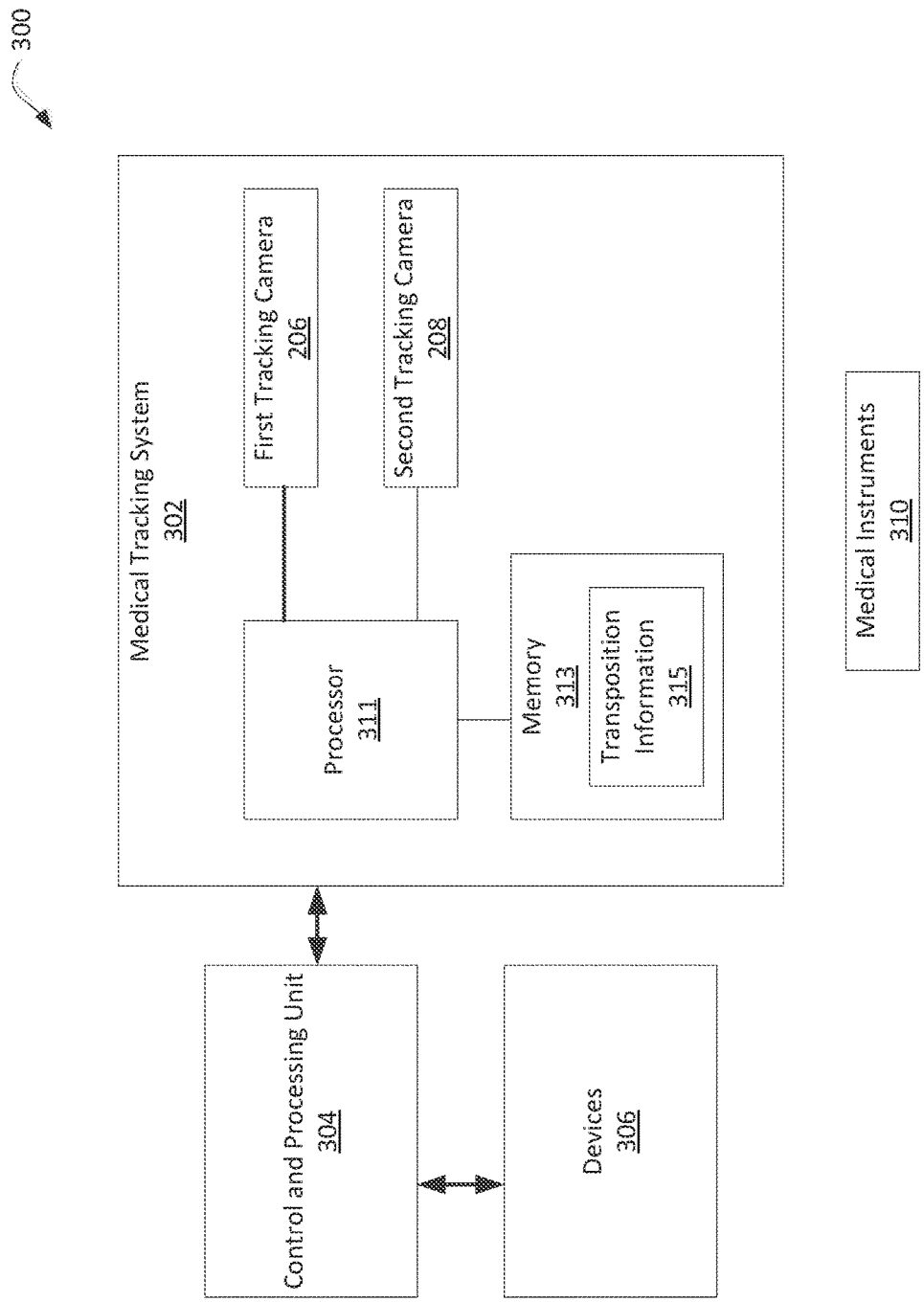
FIG. 3 is a block diagram of example components of a medical electronic device in accordance with example embodiments of the present disclosure.

Referring now to FIG. 3, a block diagram is shown illustrating a medical electronic device 300 that includes a medical tracking system 302. The medical electronic device 300 may, for example, be a medical navigation system.

In the example illustrated, the medical electronic device 300 includes a control and processing unit 304. The control and processing unit 304 may include various components including, for example, one or more processors, a memory, a system bus, one or more input/output interfaces, a communication interface, and a storage device. The control and processing unit 304 may be interfaced with other external devices, such as the medical tracking system 302 and other devices 306. The other devices 306 may include, for example, data storage, and external user input and output devices, which may include, for example, one or more of a display, keyboard, mouse, sensors attached to medical equipment, a foot pedal, and microphone and speaker. Data storage may be any suitable data storage device, such as a local or remote computing device (e.g. a computer, hard drive, digital media device, or server) having a database stored thereon.

Medical instruments 310 are identifiable by the medical electronic device 300. The medical instruments 310 may be connected to and controlled by control and processing unit 304, or medical instruments 310 may be operated or otherwise employed independent of control and processing unit 304. The medical tracking system 302 may be employed to track one or more of medical instruments 310 (such as the tracked instruments described above) and spatially register the one or more tracked instruments to an intraoperative reference frame. For example, medical instruments 310 may include tracking markers such as tracking spheres that may be recognizable by a tracking system provided by the medical tracking system 302.

The control and processing unit 304 may also interface with a number of configurable devices, and may intraoperatively reconfigure one or more of such devices based on configuration parameters obtained from configuration data. Examples of devices include one or more external imaging devices, one or more illumination devices, an automated arm, one or more projection devices, one or more 3D scanning devices, (such as CT, MRI, or structured light) and one or more displays. Examples of external imaging devices include OCT imaging devices and ultrasound imaging devices.

The control and processing unit 304 interfaces with a medical tracking system 302. The medical tracking system 302 includes a first tracking system 206 and a second tracking system 208. The first tracking system 206 and the second tracking system 208 may be of the type described above with reference to FIG. 2. The first tracking system 206 and the second tracking system 208 are coupled to a processor 311. The processor 311 may be configured to track the tracked instrument using data from the first tracking system 206 and data from the second tracking system 208.

The processor 311 is coupled with memory 313. The memory may be of various types. While a single memory is illustrated in FIG. 3, the memory may be comprised of a plurality of memory components, each suited for different purposes.

The memory may include a data storage device which may store transposition information 315. The transposition information 315 maps data received from the first tracking system and the second tracking system onto a common space. For example, the transposition information 315 may map a viewspace of the second tracking system to a viewspace of the first tracking system By way of further example, the transposition information 315 may map a viewspace of the second tracking system to a patient reference space, which is a space defined based on a location of a patient. As will be described in greater detail below, in at least some embodiments, the processor 311 may be configured to determine such transposition information at to store the transposition information in the memory 313.

Exemplary aspects of the disclosure can be implemented via processor(s) (such as the processor 311 of the medical tracking system 302 and/or a processor of the control and processing unit 304)) coupled with memory. For example, the functionalities described herein can be partially implemented via hardware logic in a processor and partially using the instructions stored in memory, as one or more processing modules or engines.

Some embodiments may be implemented using a processor without additional instructions stored in memory. Some embodiments may be implemented using the instructions stored in memory for execution by one or more general purpose microprocessors.

While some embodiments can be implemented in fully functioning computers and computer systems, various embodiments are capable of being distributed as a computing product in a variety of forms and are capable of being applied regardless of the particular type of machine or computer readable media used to actually effect the distribution.

Figure 4:
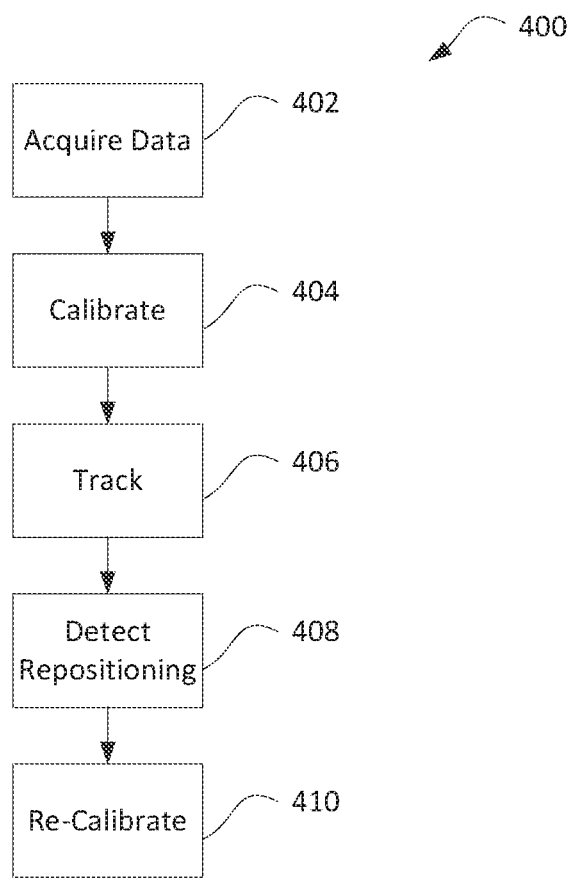
FIG. 4 is a flowchart illustrating a method of tracking a medical instrument in accordance with example embodiments of the present disclosure.

Reference will now be made to FIG. 4 which illustrates a flowchart of an example method 400 of tracking a medical instrument, such as the tracked instrument of FIG. 2. The method may be performed by a processor associated with a medical electronic device such as a processor provided on a medical tracking system 302 and/or a processor of the control and processing unit 304. In some embodiments, the method may be performed by multiple processors. In at least some embodiments, a computer readable storage medium, such as a processor, may include processor-executable instructions which, when executed, configure a processor to perform the method 400 of FIG. 4.

At operation 402, the first tracking system and the second tracking system acquire data, which is then provided to and received by the processor. That is, the tracking systems attempt to track tracking markers such as tracking markers provided on a tracked instrument.

At operation 404, the processor calibrates tracking systems. More particularly, the processor determines, based on data received from the first tracking system and data received from the second tracking system, transposition information 315 (FIG. 3) to map data received from the first tracking system and data received from the second tracking system to a common space.

In some embodiments, the transposition information transposes a location of a tracked instrument in a second space associated with the second camera to a first space associated with the first tracking system. That is, in at least some embodiments, the first tracking system acts as a primary tracking system and the second tracking system acts as a supplementary tracking system. In such embodiments, a coordinate system may be defined with reference to the first tracking system and data associated with the second camera may be mapped to that coordinate system.

The transposition information may, in some embodiments, be determined using data from the first tracking system and data from the second camera that is obtained when a tracked instrument is within both a first tracking region associated with the first tracking system and a second tracking region associated with a second tracking system. That is, a tracked instrument itself may be used, in some embodiments, in order to calibrate the tracked cameras by determining the transposition information. During calibration, features of the tracked instrument represented in data obtained by the first tracking system may be compared with features of the tracked instrument represented in data obtained by the second tracking system. More particularly, the position of a tracked instrument in a first space associated with a first tracking marker and the position of a tracked instrument in a second space associated with a second tracking marker are determined. The transposition information may be determined based on these positions.

For example, the transposition information may represent a transposition that may be applied to the position of a tracking marker in a second space (such as a coordinate system associated with the second tracking system) to transpose it to a first space (such as a coordinate system associated with the first tracking system).

The data from the first tracking system and the data from the second tracking system that are used to determine the position of the tracked instrument are received at substantially the same time to reduce errors from movements of the tracked instrument. In at least some embodiments, the data from the first tracking system and the data from the second tracking system may include respective time stamps or other timing information which indicates the time that such data was acquired. These time stamps may be provided based on synchronized clocks. In such embodiments, the processor may, during calibration, temporally relate data received from the first tracking system with data received from the second tracking system. That is, the processor may identify data from the first tracking system acquired at approximately the same time as other data from the second tracking system.

Thus, in some embodiments, calibration may be performed during operation 404 by identifying common tracking markers in data associated with a first tracking system and data associated with a second tracking system. Such common tracking markers may be the tracking markers on the tracked instrument or they may be tracking markers provided elsewhere (i.e., apart from the tracked instrument). For example, in some embodiments, a plurality of reference tracking markers may be fixedly positioned in a medical procedure room within the first tracking region associated with the first tracking system and the second tracking region associated with the second tracking system. In such embodiments, transposition information may be determined by identifying the reference tracking markers in data received from the first tracking system and in data received from the second tracking system. That is transposition information may be obtained which transposes the position of these tracking markers for each tracking system to a common space.

Calibration may also be performed using differing tracking markers and based on previously determined orientation information defining the relative position of these tracking markers in space. For example, a first tracking system may observe a first tracking marker that is fixedly positioned relative to a second tracking marker that is observed by a second tracking system. Transposition information may be obtained by identifying the first tracking marker in data received from the first tracking system and the second tracking marker in data received from the second tracking system and also based on the orientation information defining the relative positions of the first and second tracking markers.

Figure 5:
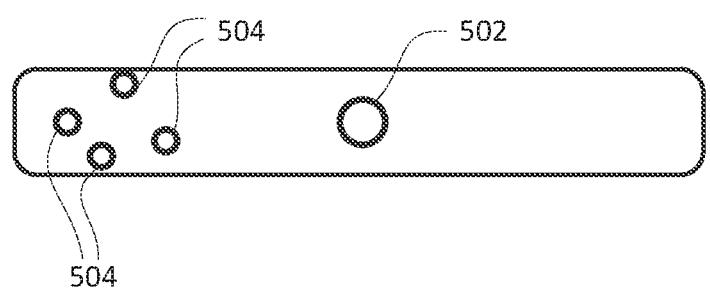
FIG. 5 is a front view of an example tracking system.

Further, in some embodiments, transposition information may not be obtained by identifying common tracking markers in data from the first tracking system and data from the second tracking system. Instead, transposition information may be obtained by identifying other features in data from one or more of the tracking systems. For example, referring briefly to FIG. 5, a front view of an example tracking system is illustrated. More particularly in the illustrated embodiment, a tracking system 502 of the type described above has a plurality of tracking markers 504 fixedly connected thereto. The tracking markers 504 are located in a known pattern relative to the tracking system. The tracking markers 504 may, for example, be on a front side of a tracking system 502 (which may be a lens side), a back side of the tracking system 502, etc. By way of further example, the tracking markers 504 may be affixed to a fixture that holds them away from the tracking system 502 at a known relative position. Such fixed tracking markers may also be used by the medical tracking system to determine the transposition information.

For example, referring again to FIG. 4, the first tracking system may have a plurality of tracking markers fixedly connected thereto. These tracking markers may be located within the second tracking region (i.e., within a space that is observable by the second tracking system). In such embodiments, during operation 404, the processor determines the transposition information by identifying, based on the data received from the second tracking system, a location of the tracking markers fixedly connected to the first tracking system. Using this location information, and previously stored data (which may be stored in memory of the medical electronic device) regarding the spatial separation between the tracking markers and the first tracking system, the transposition information may be determined. For example, the processor may use the information to effectively determine the location of the first tracking system relative to the second. Understanding the relationship between the locations of the tracking systems allows transposition information to be obtained by the processor.

After calibration, the processor may track the tracked instrument at operation 406. The tracking of the tracked instrument may, at any given time, rely on data from the first tracking system, data from the second tracking system, or data from both the first tracking system and the second tracking system. For example, when the tracked instrument is not represented in the data from the first tracking system (e.g., when the tracked instrument is blocked by an operator) but is represented in the data from the second tracking system, the processor may use the data from the second tracking system and the transposition information to determine the position of the tracked instrument in the common space described above with respect to operation 404.

When the tracked instrument is represented in both the data from the first tracking system and the data from the second tracking system, the processor may, in some embodiments, determine the position of the tracked instrument in the common space based on the data from the first camera, the data from the second camera and the transposition information. That is, in at least some embodiments, when the tracked instrument is visible to both tracking systems, data from both tracking systems may be used to determine the position of the tracked instrument. In some embodiments, when the tracked instrument is visible to both tracking systems, the processor determines a position of a tracked instrument within the first tracking region using data from the first tracking system and determines the position of the tracked instrument within the first tracking region using data from the second tracking system. This data may be combined to determine the predicted location of the tracked instrument. In some embodiments a positional estimation algorithm may be used to determine the position of a tracked instrument. For example, in some embodiments, a Kalman filter may be used to identify the position of the tracked instrument. In some embodiments, after transposition information is obtained, the processor may generate a Bayesian map of confidence and accuracy ranges for the tracked instrument.

During operation 406, timing information such as time stamps that represent the currency of data obtained by the first tracking system may be related to similar timing information for the second tracking system. That is, the processor may temporally relate data received from the first tracking system with data received from the second tracking system based on the time stamps. The time stamps are applied to the data at the time of data capture to ensure that delays introduced by cabling, etc., do not introduce analysis error.

In some embodiments, at operation 408, the processor may detect repositioning of one of the tracking systems. For example, in some embodiments, the medical electronic device may automatically detect re-positioning of the second tracking system in the medical procedure room. For example, when the processor determines that a location of a tracked instrument (or tracking markers provided elsewhere) that is determined based on data from the first tracking system is different than the location of the tracked instrument (or tracking markers provided elsewhere) that is determined based on data from the second tracking system, the processor may determine that one of the tracking systems has been re-positioned.

In embodiments in which tracking markers are fixed in known spaced relation to a tracking system (such as the embodiment of FIG. 5), re-positioning may be detected when the location of those tracking markers changes in the data obtained by a tracking system that is positioned to observe such tracking markers. For example, when the second tracking system is positioned to observe tracking markers that are fixed to the first tracking system and the position of those tracking markers in a viewspace of the second tracking system suddenly changes, the medical electronic device may determine that the second tracking system has been repositioned.

When re-positioning is detected, the processor, at operation 410, automatically recalibrates. That is, the processor automatically re-determines transposition information. This transposition information is determined from further data received from the second tracking system. The further data is data that is received after the re-positioning.

After re-calibration, the processor may resume tracking at operation 406.

Figure 6:
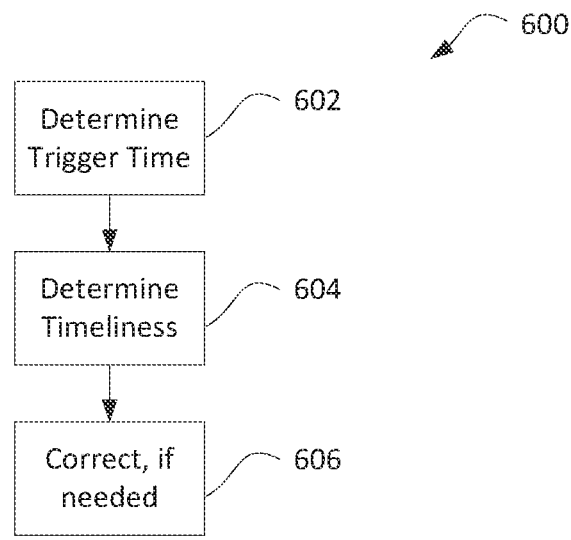
FIG. 6 is a flowchart illustrating a method of monitoring timeliness in accordance with example embodiments of the present disclosure.

Reference will now be made to FIG. 6 which illustrates a flowchart of an example method 600 of monitoring timeliness of tracking system data. The method 600 may be performed by a processor associated with a medical electronic device such as a processor provided on a medical tracking system 302 and/or a processor of the control and processing unit 304. In some embodiments, the method may be performed by multiple processors. In at least some embodiments, a computer readable storage medium, such as a processor, may include processor-executable instructions which, when executed, configure a processor to perform the method 600 of FIG. 6.

As noted above, when relying on multiple cameras, an error can sometimes occur when data from one tracking system is analyzed together with data from another of the tracking systems that was obtained at a different time. More particularly, since a scene in a medical procedure room may change quickly, an analysis error could occur when data from differing times are used to locate a tracked instrument. In at least some embodiments, the medical electronic device may be configured to monitor the timeliness of data to reduce or prevent the occurrence of such errors.

In at least some embodiments, the tracking systems may be infrared (IR) tracking systems which include respective emitters. The emitters may be configured to periodically emit radiation. For example, an emitter associated with the first tracking system may be configured to periodically emit radiation in the first tracking region. Such tracking systems may track the tracked instrument based on light reflected from the tracking markers on the tracked instrument after the emission of the radiation.

In some embodiments, at least one of the tracking systems may be pointed at another of the tracking systems. For example, the second tracking system may be directed at the first tracking system. That is, the first tracking system may be located within the second tracking region. In such embodiments, the second tracking region may be able to determine when the emitter associated with the first tracking system has triggered. Accordingly, in at least some embodiments, at operation 602, the processor determines a time at which the emitter was triggered based on data received from the second tracking system.

At operation 604, the processor may determine timeliness information based on the time at which the emitter was triggered. For example, in some embodiments, the first tracking system may be configured to trigger according to a predefined period. From this period, a scheduled time at which the first tracking system should have been triggered may be determined. In at least some embodiments, at operation 604, the processor may determine whether the first tracking system was triggered at the expected time based on the time at which the emitter was triggered and the scheduled time. In at least some embodiments, the period at which the first tracking system is to be triggered is based on the time at which the second tracking system is to be triggered. For example, the tracking systems may be configured to be triggered successively at a short interval. This ensures that the tracking systems are not triggered at the same time (which could cause interference due to the multiple light sources for the multiple emitters) but that they are triggered at similar times to one another. Thus, in some embodiments, at operation 604, the processor may determine whether the first tracking system was triggered at an appropriate time period following the triggering of the second tracking system. The appropriateness of the time period may be evaluated according to predefined criteria (such as a range) stored in memory, for example.

If, at operation 604, it is determined that the emitter was not triggered at the expected time, the processor may apply a correction at operation 606. For example, in some embodiments, at operation 606, the processor may adjust a clock associated with the first tracking system so that it will trigger at different times in the future. For example, the processor may introduce a delay in the triggering of the first tracking system.

Figure 7:
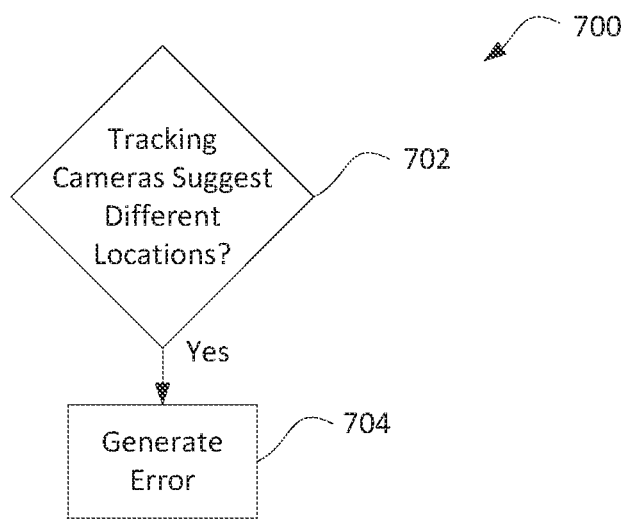
FIG. 7 is a flowchart illustrating a method for identifying a camera error in accordance with example embodiments of the present disclosure.

Reference will now be made to FIG. 7 which illustrates a flowchart of an example method 700 for identifying a camera error. In the embodiment of FIG. 7, the medical electronic device may include a third tracking system in addition to the first and second tracking systems. The third tracking system is providing a third tracking region.

The method 700 of FIG. 7 may be performed by a processor associated with a medical electronic device such as a processor provided on a medical tracking system 302 and/or a processor of the control and processing unit 304. In some embodiments, the method may be performed by multiple processors. In at least some embodiments, a computer readable storage medium, such as a processor, may include processor-executable instructions which, when executed, configure a processor to perform the method 700 of FIG. 7.

Prior to the operation of the method 700 of FIG. 7, the tracking systems may have been calibrated using techniques discussed herein such that transposition information maps data obtained at the first tracking system, second tracking system and third tracking system to a common space.

At operation 702, the processor determines whether a tracking system has a failure. More particularly, the processor identifies a failure of one of the first, second or third tracking systems when that tracking system suggests that a tracked instrument is in a location that is different from the location suggested by the other tracking systems. If one of the cameras suggests a location that is different than the location suggested by the other two cameras, then the processor may determine that a tracking system has failed and may generate an error at operation 704.

The error may, for example, be an audible or visual error to an operator of the medical electronic device. In some embodiments, the error may trigger remedial action from the medical electronic device. For example, re-calibration may be automatically performed and/or the medical electronic device may begin to disregard data from the affected camera. In some embodiments, the error may not be an audible or visual alert and may, instead, be remedial action performed by the medical electronic device. For example, the medical electronic device may ignore data from the affected camera or may de-weight the importance of such data relative to the weighted importance of other data (e.g., data for other tracking systems).

Similar techniques to those described above may be used, in some embodiments, to provide a tracking system using two or more image sensors that are movable relative to one another. More particularly, a tracking system having multiple image sensors may be installed on site in a medical procedure room. The image sensors may be infrared camera. Such image sensors may be fixedly positioned in the medical procedure room or movable within the medical procedure room. A tracking system may be configured to automatically calibrate when such image sensors are re-positioned. For example, referring now to FIG. 8, a block diagram is shown illustrating a tracking system 802.

In the example illustrated, the tracking system 802 includes a first image sensor 804 and a second image sensor 806. The first image sensor 804 and the second image sensor 806 are coupled to a processor 811. The processor 811 may be configured to track a tracked instrument using data from the first image sensor 804 and data from the second image sensor 806.

Figure 8:
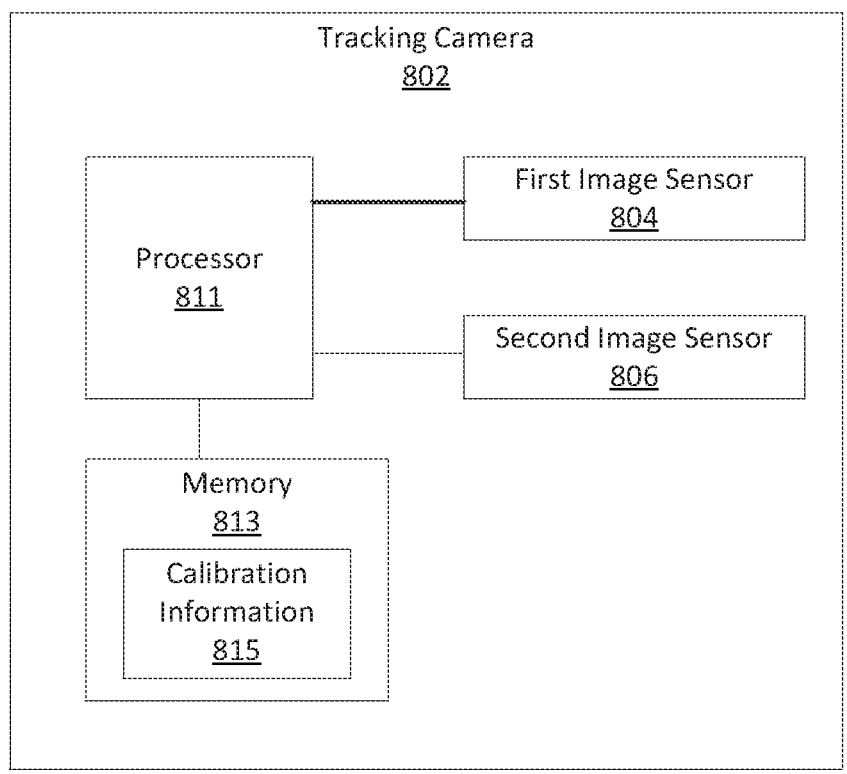
FIG. 8 is a block diagram of an example tracking camera in accordance with example embodiments of the present disclosure.

The processor 811 is coupled with memory 813. The memory may be of various types. While a single memory is illustrated in FIG. 8, the memory may be comprised of a plurality of memory components, each suited for different purposes.

The memory may include a data storage device which may store calibration information 815. The calibration information 815 is information regarding the current position of the first image sensor 804 and the current position of the second image sensor 806. As will be described in greater detail below, in at least some embodiments, the processor 811 may be configured to determine such calibration information and to store the calibration information in the memory 813.

The calibration information may be determined in the manner that the transposition information is determined, as described above with reference to FIG. 4. For example, the processor receives data acquired by the first image sensor and the second image sensor and identifies common features (such as common tracking markers) in such data. Based on this information, calibration information may be determined. The calibration information represents the relative location of the first image sensor and the second image sensor.

Accordingly, multiple image sensors may be used to effectively form a tracking system on-site. Such standalone image sensors (i.e., image sensors that are not assembled into a tracking system during manufacture) may also be used to enhance the capabilities of a tracking system. That is, such standalone image sensors may be used to provide an improved tracking system. In such embodiments, medical electronic device may include a tracking system that is manufactured to include two or more image sensors and also a standalone image sensor. The standalone image sensor may be movable relative to the tracking system. The medical electronic device may be configured to automatically determine the calibration information for the standalone image sensor based on data from the standalone image sensor and data from the tracking system. That is, common features represented in the data from the standalone image sensor and the data from the tracking system may be identified in order to calibrate the standalone image sensor (i.e., in order to determine calibration information that aids in mapping objects represented in an image obtained at the standalone image sensor and objects represented in data of the tracking system to a common space).

A computer processor, or just "processor", is a hardware device for performing digital computations. It is the express intent of the inventors that a "processor" does not include a human; rather it is limited to be an electronic device, or devices, that perform digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

Multiple computers (also referred to as computer systems, computing devices, clients and servers) may be networked via a computer network, which may also be referred to as an electronic network or an electronic communications network. When they are relatively close together the network may be a local area network (LAN), for example, using Ethernet. When they are remotely located, the network may be a wide area network (WAN), such as the internet, that computers may connect to via a modem, or they may connect to through a LAN that they are directly connected to.

Computer-readable memory, which may also be referred to as a computer-readable medium or a computer-readable storage medium, which terms have identical (equivalent) meanings herein, can include any one or a combination of non-transitory, tangible memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.) Memory may employ electronic, magnetic, optical, and/or other technologies, but excludes transitory propagating signals so that all references to computer-readable memory exclude transitory propagating signals. Memory may be distributed such that at least two components are remote from one another, but are still all accessible by one or more processors. A nonvolatile computer-readable memory refers to a computer-readable memory (and equivalent terms) that can retain information stored in the memory when it is not powered. A computer-readable memory is a physical, tangible object that is a composition of matter. The storage of data, which may be computer instructions, or software, in a computer-readable memory physically transforms that computer-readable memory by physically modifying it to store the data or software that can later be read and used to cause a processor to perform the functions specified by the software or to otherwise make the data available for use by the processor. In the case of software, the executable instructions are thereby tangibly embodied on the computer-readable memory. It is the express intent of the inventor that in any claim to a computer-readable memory, the computer-readable memory, being a physical object that has been transformed to record the elements recited as being stored thereon, is an essential element of the claim.

Software may include one or more separate computer programs configured to provide a sequence, or a plurality of sequences, of instructions to one or more processors to cause the processors to perform computations, control other devices, receive input, send output, etc.

It is intended that the invention includes computer-readable memory containing any or all of the software described herein. In particular, the invention includes such software stored on non-volatile computer-readable memory that may be used to distribute or sell embodiments of the invention or parts thereof.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

We claim:

1. A medical tracking system for identifying a position of a tracked instrument having a plurality of tracking markers provided thereon, the medical tracking system comprising:

a first tracking system providing a first tracking region, the first tracking system configured to track the tracked instrument within the first tracking region, wherein the first tracking system includes an emitter which is triggered periodically to emit radiation in the first tracking region and wherein the first tracking system tracks the tracked instrument based on light reflected from tracking markers on the tracked instrument;

a second tracking system providing a second tracking region, the second tracking system configured to track the tracked instrument within the second tracking region, wherein the first tracking system is within the second tracking region; and a processor coupled to the first tracking system and the second tracking system, the processor configured to determine, based on data received from the first tracking system and data received from the second tracking system, transposition information to map data received from the first tracking system and data received from the second tracking system into a common space, wherein the processor is further configured to:

based on data received from the second tracking system, determine a time at which the emitter was triggered; and based on the time at which the emitter was triggered and a scheduled time, determine whether the first tracking system triggered at the expected time.

2. The medical tracking system of claim 1, wherein the first tracking system is fixedly mounted within a medical procedure room and wherein the second tracking system is moveable within the medical procedure room.

3. The medical tracking system of claim 2, wherein the processor is further configured to:

after re-positioning of the second tracking system within the medical procedure room, automatically re-determine the transposition information based on further data received from the second tracking system, the further data received after the re-positioning.

4. The medical tracking system of claim 1, wherein the processor is further configured to:

determine a position of a tracked instrument within the first tracking region using data from the first tracking system; and determine the position of a tracked instrument within the first tracking region using data from the second tracking system.

5. The medical tracking system of claim 1, wherein the transposition information transposes a location of a tracked instrument in a second space associated with the second tracking system to a first space associated with the first tracking system.

6. The medical tracking system of claim 5, wherein determining the transposition information comprises:

when the tracked instrument is within both the first tracking region and the second tracking region, determining the position of the tracked instrument in the first space based on data received from the first tracking system and determining the position of the tracked instrument in the second space based on data received from the second camera; and determining the transposition information based on the position of the tracked instrument in the first space and the position of the tracked instrument in the second space.

7. The medical tracking system of claim 1, further comprising:
a third tracking system providing a third tracking region, the second tracking system configured to track the tracked instrument within the third tracking region,
and wherein the processor is configured to determine further transposition information to map data received from the third tracking system to the common space.

8. The medical tracking system of claim 7 wherein the data from the first tracking system and the data from the second tracking system include respective time stamps and wherein the processor is further configured to temporally relate data received from the first tracking system with data received from the second tracking system based on the time stamps.

9. The medical tracking system of claim 1, wherein the first tracking system comprises a plurality of tracking markers fixedly connected thereto and located within the second tracking region and wherein determining the transposition information comprises identifying, based on the data received from the second tracking system, a location of the tracking markers fixedly connected to the first tracking system.

10. The medical tracking system of claim 1, wherein the transposition information maps a viewspace of the second tracking system to a viewspace of the first tracking system.

11. The medical tracking system of claim 1, wherein the processor is further configured to:
when the tracked instrument is not represented in the data from the first tracking system but is represented in the data from the second tracking system, use the data from the second tracking system and the transposition information to determine the position of the tracked instrument in the common space.

12. The medical tracking system of claim 1, wherein the processor is further configured to:
when the tracked instrument is represented in the data from the first tracking system and is also represented in the data from the second tracking system, determine the position of the tracked instrument in the common space based on the data from the first tracking system, the data from the second tracking system and the transposition information.

13. The medical tracking system of claim 12, wherein the position of the tracked instrument is determined using a positional estimation algorithm.

14. The medical tracking system of claim 1, further comprising a plurality of reference tracking markers fixedly positioned in a medical procedure room within the first tracking region and the second tracking region and wherein the transposition information is determined by identifying the reference tracking markers in data received from the first tracking system and in data received from the second tracking system.

15. The medical tracking system of claim 1, wherein the processor is further configured to, after determining the transposition information, generate a Bayesian map of confidence and accuracy range for the tracked instrument.

16. The medical tracking system of claim 1, further comprising a third tracking system providing a third tracking region and wherein the processor is coupled to the third tracking system and is further configured to:

identify a failure of one of the first, second or third tracking systems when that tracking system suggests the tracked instrument is in a location that is different from the location suggested by the other of the tracking systems.

17. A processor coupled with a first tracking system and a second tracking system, the processor configured to:
receive data from the first tracking system, the first tracking system providing a first tracking region and the first tracking system configured to track a tracked instrument within the first tracking region, wherein the first tracking system includes an emitter which is triggered periodically to emit radiation in the first tracking region and wherein the first tracking system tracks the tracked instrument based on light reflected from tracking markers on the tracked instrument;
receive data from the second tracking system, the second tracking system providing a second tracking region, the second tracking system configured to track the tracked instrument within the second tracking region, wherein the first tracking system is within the second tracking region;
determine, based on data received from the first tracking system and data received from the second tracking system, transposition information to map data received from the first tracking system and data received from the second tracking system into a common space;
determine, based on data received from the second tracking system, a time at which the emitter was triggered; and
determine, based on the time at which the emitter was triggered and a scheduled time, whether the first tracking system triggered at the expected time.

18. A non-transitory computer readable storage medium comprising computer-executable instructions which, when executed, configure a processor to:
receive data from a first tracking system, the first tracking system providing a first tracking region and the first tracking system configured to track a tracked instrument within the first tracking region, wherein the first tracking system includes an emitter which is triggered periodically to emit radiation in the first tracking region and wherein the first tracking system tracks the tracked instrument based on light reflected from tracking markers on the tracked instrument;
receive data from a second tracking system, the second tracking system providing a second tracking region, the second tracking system configured to track the tracked instrument within the second tracking region, wherein the first tracking system is within the second tracking region;
determine, based on data received from the first tracking system and data received from the second tracking system, transposition information to map data received from the first tracking system and data received from the second tracking system into a common space;
determine, based on data received from the second tracking system, a time at which the emitter was triggered; and
determine, based on the time at which the emitter was triggered and a scheduled time, whether the first tracking system triggered at the expected time.

* * * * *